(12) United States Patent
Neuberger

(10) Patent No.: US 6,383,179 B1
(45) Date of Patent: May 7, 2002

(54) DIODE LASER SCALPEL

(75) Inventor: Wolfgang Neuberger, F.T Labuan (MY)

(73) Assignee: CeramOptec Industries Inc., East Longmeadow, MA (US)

( * ) Notice: Subject to any disclaimer, the term of this patent is extended or adjusted under 35 U.S.C. 154(b) by 0 days.

(21) Appl. No.: 09/372,541

(22) Filed: Aug. 11, 1999

(51) Int. Cl.⁷ .............................................. A61B 18/18
(52) U.S. Cl. ........................ 606/16; 606/167; 606/170; 606/13
(58) Field of Search ............................... 606/10, 13–16, 606/41, 45, 161, 167–170, 173; 128/898

(56) References Cited

U.S. PATENT DOCUMENTS

| | | | |
|---|---|---|---|
| 4,273,127 A | * 6/1981 | Auth | 128/303.1 |
| 4,314,559 A | * 2/1982 | Allen | 128/303.14 |
| 4,627,435 A | 12/1986 | Hoskin | |
| 5,154,708 A | * 10/1992 | Long et al. | 606/16 |
| 5,303,324 A | 4/1994 | Lundahl | 385/147 |
| 5,324,299 A | 6/1994 | Davison et al. | |
| 5,330,465 A | * 7/1994 | Doiron et al. | 606/7 |
| 5,348,552 A | * 9/1994 | Nakajima | 606/13 |
| 5,366,456 A | 11/1994 | Rink et al. | |
| 5,498,260 A | * 3/1996 | Rink et al. | 606/16 |
| 5,520,681 A | * 5/1996 | Fuller et al. | 606/17 |
| 5,553,629 A | * 9/1996 | Keipert et al. | 128/898 |
| 5,571,098 A | 11/1996 | Domankevitz et al. | |

FOREIGN PATENT DOCUMENTS

| | | | | |
|---|---|---|---|---|
| DE | 29-35141 A1 | * | 8/1979 | B05D/07/02 |
| JP | 02-240605 A | * | 9/1990 | G02B/06/10 |

* cited by examiner

*Primary Examiner*—Linda C. M. Dvorak
*Assistant Examiner*—Ahmed Farah
(74) *Attorney, Agent, or Firm*—Bolesh J. Skutnik; B J Associates

(57) ABSTRACT

A device that simultaneously incises an area and cauterizes the desired tissue. The device incorporates laser energy by some means into a mechanical scalpel so that the incised area is cauterized as well. For example, a laser source is coupled by some means to an optically transparent blade such as a diamond knife. The diamond knife is appropriately coated so that radiation only exits at desired areas. In another example, optical fibers are embedded into a sharp edge blade scalpel with means to couple to a suitable radiation source.

18 Claims, 5 Drawing Sheets

DIODE LASER SCALPEL

BACKGROUND OF THE INVENTION

1. Field of the Invention

The present invention relates to surgical incision instruments such as scalpels. In particular this invention relates to scalpels that incorporate a laser.

2. Invention Disclosure Statement

Scalpels are an important basic tool used in surgical operations. However scalpels create an undesired flow of blood from the cut tissue area. Means to reduce blood flow and cauterize tissue are advantageous to the patient's health as well as to provide the surgeon with an unobstructed view of the incised tissue. The most common method applied to reduce blood flow is heat-induced coagulation following a sharp edge scalpel incision. In addition to typical sharp edge mechanical scalpels, laser and ultrasonic scalpels are also available to make incisions. Prior art patents propose several ways to induce coagulation in conjunction with cutting. Laser and ultrasonic methods are an improvement over standard blade scalpels, but still these methods have only limited coagulating abilities. The use of an optical fiber to cauterize an area is problematic because optical fibers are difficult to drag through tissue and the hand-pieces that incorporate optical fibers are often unwieldy.

U.S. Pat. No. 5,366,456 describes a coagulating scalpel that uses a laser to cut through tissue. The described device is held above the area to be incises and does not contact the treatment area. This device uses the laser energy to cut as well as cauterize the tissue. The drawback to this device however, is that surgeons are generally accustomed and familiar with the tactile feedback that a standard blade scalpel provides.

U.S. Pat. No. 5,324,299 describes an ultrasonic scalpel. This type of blade generally vibrates at a rate of around 55,000 times per second. This vibration generates ultrasound waves that change the nature of the proteins in the tissue. This device in practice however, has only limited coagulating ability.

U.S. Pat. No. 4,627,435 describes a diamond knife coupled to a laser source. The radiation energy is used to heat the blade which cauterizes the tissue. This requires that the blade be heated to temperatures between 300–500° C. This device is limited, because the entire blade and incision area is heated. This heating could cause undesired damage to tissue. Furthermore, using this device, it is not possible to cauterize only a specific area.

U.S. Pat. No. 5,571,098 describes a laser surgical device. This device is comprised of a mechanical cutting instrument such as a sharp edge scalpel, and an optical fiber attached to the handle area. Radiation is directed from the distal end of the handle to the incision area. The optical fiber allows radiation to be applied to tissue before the incision is made and therefore cauterize the tissue to be incised. A drawback to this invention is that the externally connected fiber can interfere with the use of the scalpel and make it difficult to control the incision area.

The present invention gives the benefits of a laser incision, while still providing the operator with tactile feedback. The present invention is also easier to use since the optical fiber is incorporated into the handle of the device. The problems with the prior art are overcome in these ways by the present invention.

BRIEF SUMMARY OF THE INVENTION

It is an object of the present invention to provide a scalpel that can cut as well as cauterize tissue.

It is another object of the present invention to provide a laser scalpel that is easy to use and provides the operator with tactile feedback.

It is yet another object of the present invention to provide a scalpel that introduces minimum trauma.

Briefly stated the present invention provides a device that simultaneously incises an area and cauterizes the desired tissue. The device incorporates laser energy by some means into a mechanical scalpel so that the incised area is cauterized as well. For example, a laser source is coupled by some means to an optically transparent blade such as a diamond knife or quartz glass knife. The diamond knife is appropriately coated so that radiation only exits at desired areas. In another example, optical fibers are embedded into a sharp edge blade scalpel with means to couple to a suitable radiation source.

The above, and other objects, features and advantages of the present invention will become apparent from the following description read in conjunction with the accompanying drawings.

DETAILED DESCRIPTION OF PREFERRED EMBODIMENTS

Prior art inventions propose several ways to cut as well as cauterize tissue with a single device. The problems with the prior art include unwieldy, difficult to use devices, limited coagulation from the device, and lack of tactile feedback. The present invention overcomes these problems and provides a surgical scalpel that gives tactile feedback to the surgeon, effectively cauterizes tissue, and is designed in a similar form to standard surgical scalpels.

In a preferred embodiment of the present invention, a scalpel has a sharp cutting edge (mechanical cutting tool) and a body incorporating some means for guiding laser light to the incision area. Appropriate means for guiding light, is optically linked to a diode laser light source. Means to direct the laser radiation into the tissue are incorporated into the device. Preferably, the radiation can be directed out from the sides of the blade (or scalpel), towards the blade's cutting edge or backward along an incision line. Preferably the wavelength of the laser radiation used is 980 nm. In alternative embodiments a wavelength between 800 and 1500 nm is used. The energy used in a preferred embodiment of the present invention is between 1 W and 10 W. The laser radiation is either a continuous wave or high frequency (10 to 1000 Hz) pulses (0.05 sec to 0.5 ms).

In another embodiment of the present invention, the scalpel is comprised of an optically transparent diamond knife. A light source is optically coupled to the blade by some means such as an optical fiber. The diamond knife has a suitable coating that only allows radiation to exit at desired areas. Alternatively the scalpel is designed to allow the blade to be interchangeable. In this embodiment different blades have different coated areas so that the area of desired cauterization can be altered.

In another embodiment, the scalpel is comprised of a common sharp edge blade that has an optical wave guide incorporated/ embedded into the blade. Alternatively the scalpel blade has multiple fibers embedded into the blade with the distal end of the fibers at various locations on the blade. In this latter embodiment, the direction of the radiation can be chosen by illuminating only the appropriate fiber.

Figure 1:
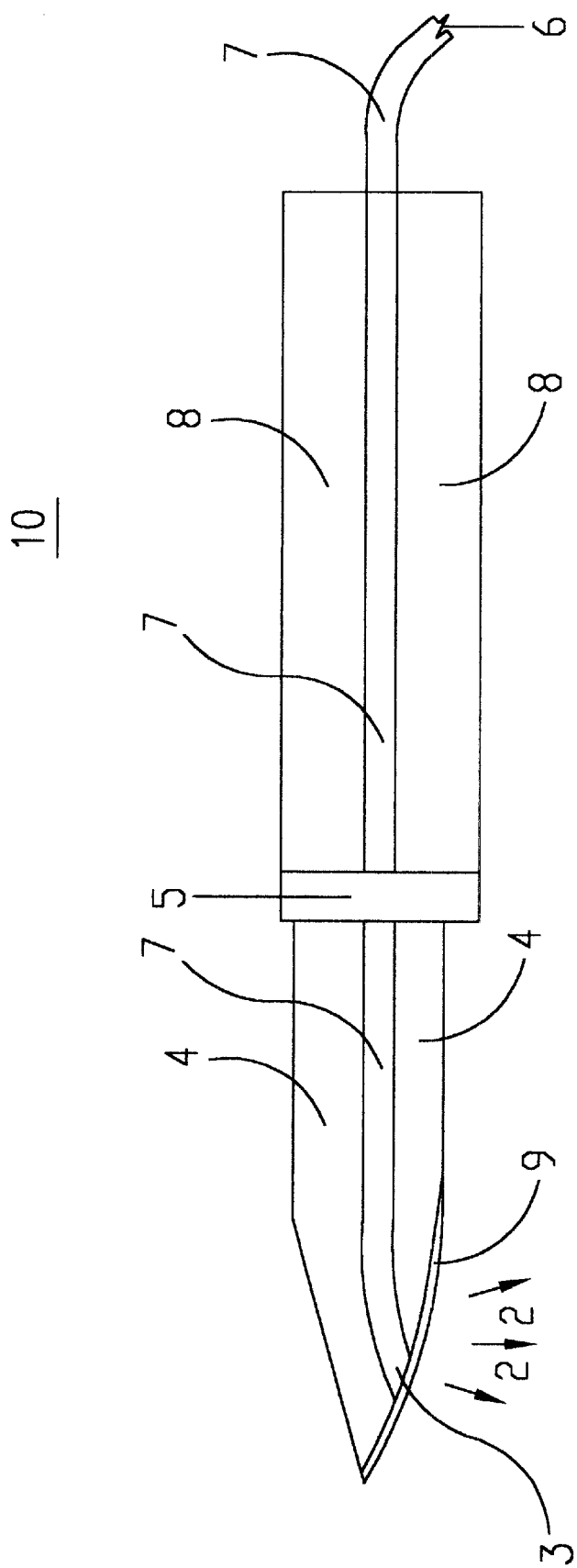
FIG. 1 depicts a cross sectional view a present invention scalpel with a optical fiber incorporates into a metal cutting edge.

FIG. 1 depicts an embodiment of the present invention that has a sharp metal scalpel blade with an embedded optical fiber. Optical fiber 7 is imbedded within scalpel handle 8 and scalpel blade 4. A suitable light source, preferably a diode laser, is connected to proximal end 6 of optical fiber 7. Light energy travels through scalpel 10 and exits near cutting edge 9. Distal end 3 of optical fiber 7 is directed toward a area needing cauterization. Scalpel 10 is designed to direct light energy 2 from the sides of scalpel blade 4, toward cutting edge 9, or backward along an incision line. Scalpel blade 4 and scalpel handle 8 are coupled by a suitable connector 5. Alternatively, connector 5 is designed to allow scalpel blade 4 to be easily replaced either with sterile/new blades or with different types of scalpel blades. Instead of a device where the blade is permanently incorporated into the scalpel, the blades are removable. This allows for various types of special scalpel blades to be used. For example, different blades have optical fibers in different positions. This allows the surgeon to control which area of tissue is cauterized.

Figure 2:
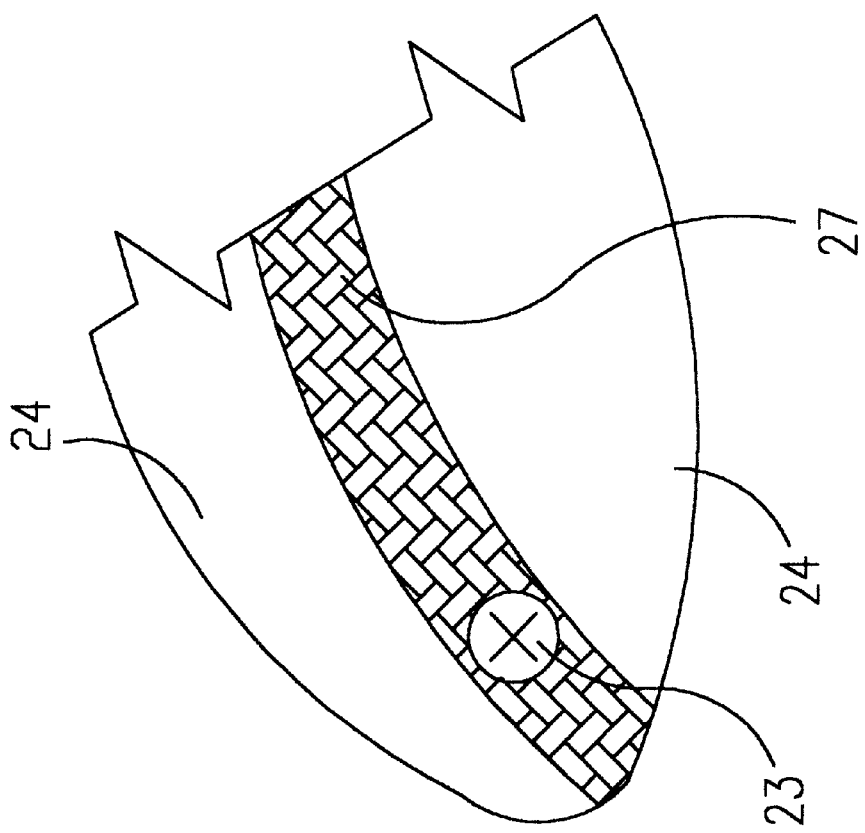
FIG. 2 depicts a side cross sectional view of one embodiment of a present invention metal blade.
Figure 3:
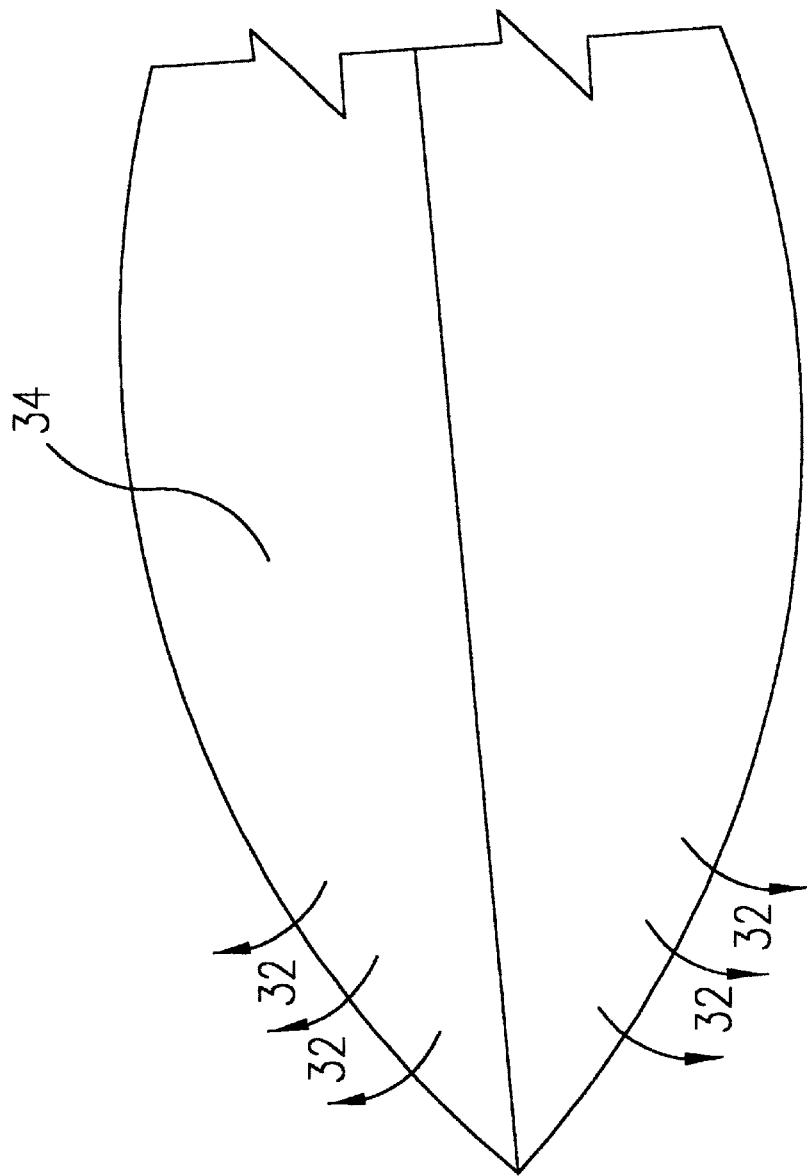
FIG. 3 shows a present invention metal blade from a top view.
Figure 4:
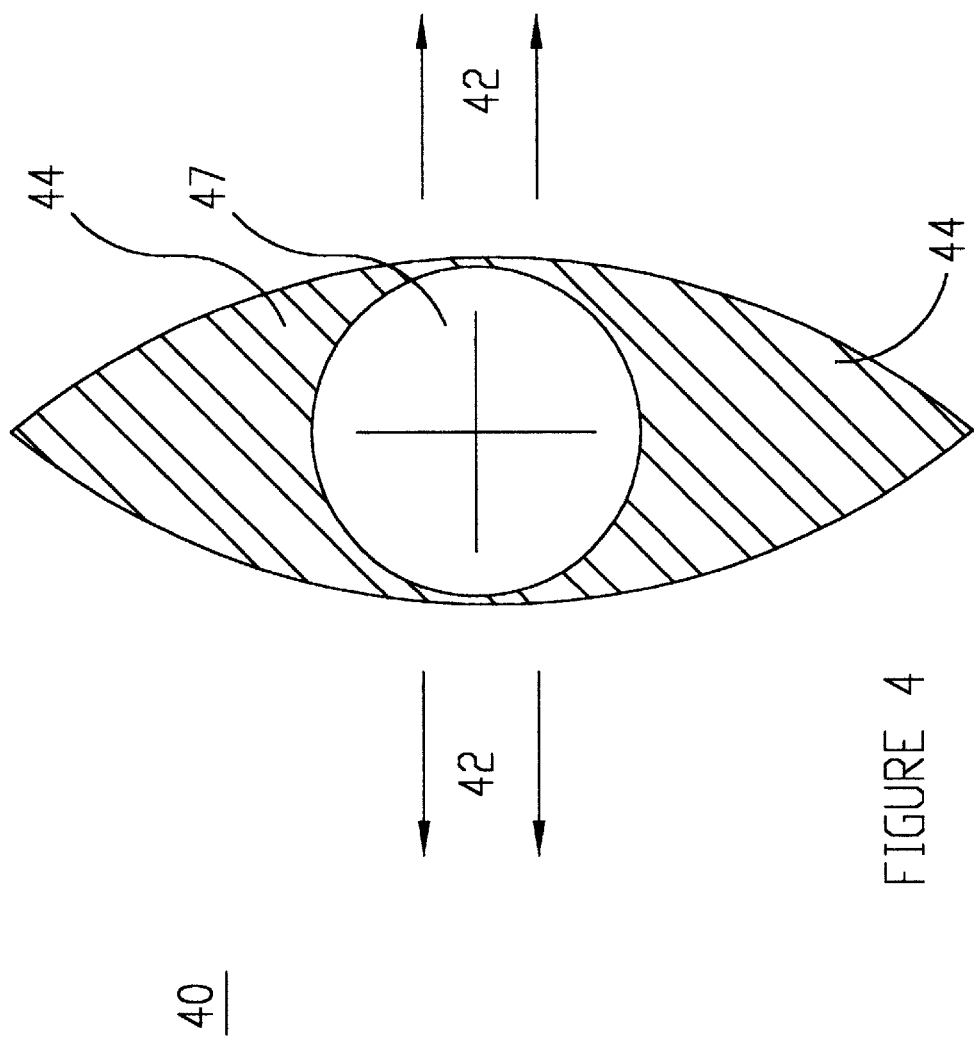
FIG. 4 depicts a cross sectional view from the front of a present invention metal blade.

FIGS. 2-4 depict a detailed view of embodiments of scalpel blade 4 in FIG. 1 from the side, top, and front respectively. FIG. 2 depicts a side cross sectional view of one embodiment of a present invention metal blade. Optical fiber 27 is embedded into metal scalpel blade 24. Light energy exits blade 20 at radiation exit area 23. FIG. 3 shows an embodiment of a present invention metal blade from a top view. Light energy 32 exits from the sides of metal scalpel blade 34. FIG. 4 depicts a cross sectional view from the front of a present invention metal blade embodiment. Optical fiber 47 is embedded in metal scalpel blade 42. Light energy 42 exits from the sides of blade 40.

Figure 5:
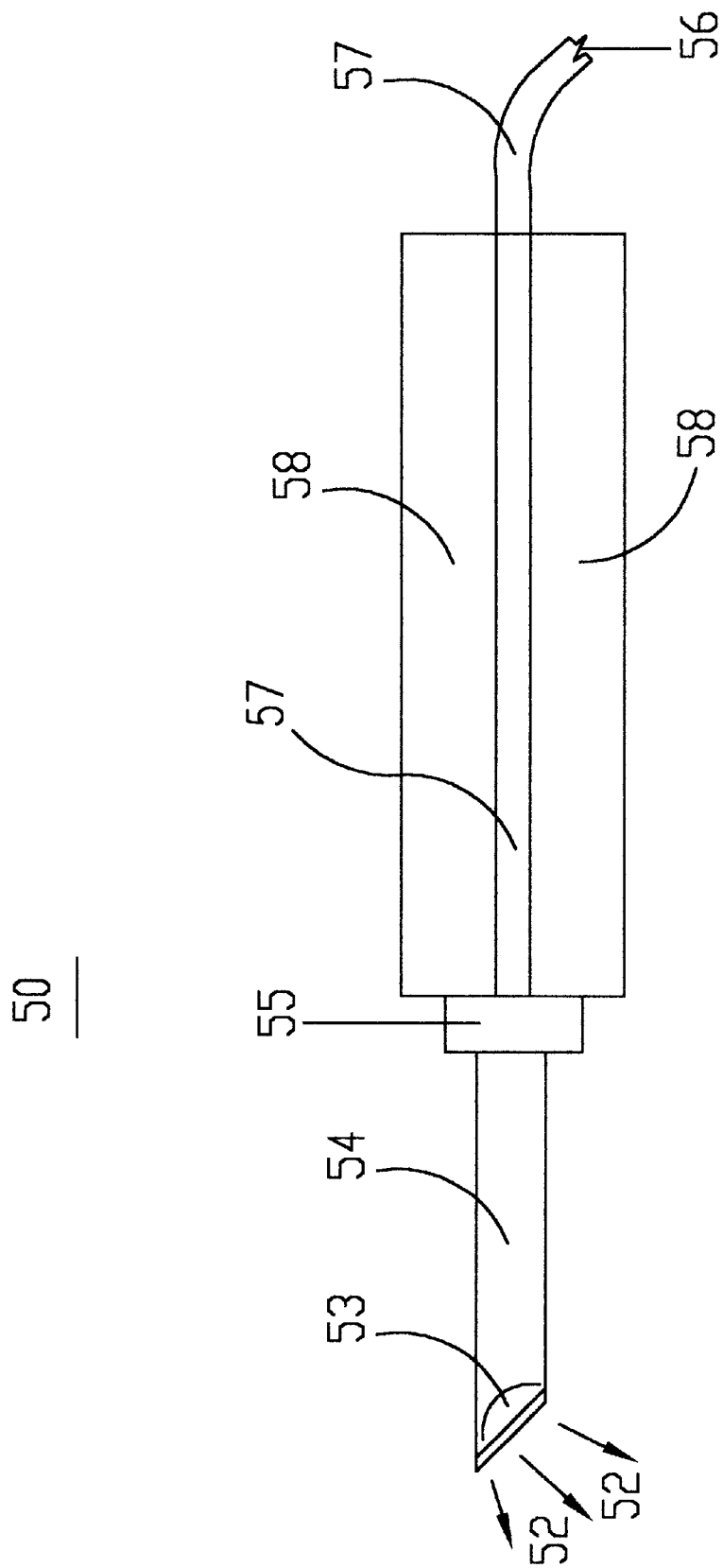
FIG. 5 shows a cross section of a present invention scalpel that incorporates a diamond knife blade.

FIG. 5 depicts another embodiment of the present invention where the scalpel blade is a diamond knife. Optical wave-guide 57 is embedded in scalpel handle 58. A suitable light source, preferably a diode laser, is connected to proximal end 56 of guide 57. Light energy travels through wave-guide 57 to scalpel blade 54. Blade 54 is specifically coated so that light only exits through desired points on the blade. Light 52 exits though distal area 53. Exit area 53 is placed so that light from scalpel 50 is directed from the sides of scalpel blade 54, toward the cutting edge, or backward along an incision line. Scalpel blade 54 and scalpel handle 58 are coupled by a suitable connector 55. Alternatively, connector 55 is designed so that scalpel blade 54 can be removed and replaced with either sterile/new blades or with different types of scalpel blades. Instead of a device where the blade is permanently incorporated into the scalpel, the blades are removable. This allows for various types of special scalpel blades to be used. For example, different blades have a coating with openings at different locations in the coating. This allows the surgeon to control which area of tissue is cauterized.

Having described preferred embodiments of the invention with reference to the accompanying drawings, it is to be understood that the invention is not limited to the precise embodiments, and that various changes and modifications may be effected therein by skilled in the art without departing from the scope or spirit of the invention as defined in the appended claims.

What is claimed is:

1. A surgical incision device to simultaneously incise and cauterize tissue comprising:

a handle;

an optically transparent sharp mechanical cutting edge;

means to couple said handle and said cutting edge to a laser source; and wherein said optically transparent cutting edge is selectively coated to allow light to exit only at desired areas of cauterization.

2. A device according to claim 1, wherein said optically transparent sharp mechanical cutting edge is a diamond knife.

3. A device according to claim 1, wherein said optically transparent sharp mechanical cutting edge is a quartz glass knife.

4. A device according to claim 1, wherein said means to couple said handle and said optically transparent sharp mechanical cutting edge to a laser source is at least one optical fiber.

5. A device according to claim 1, wherein at least one optical fiber is embedded into said handle of said surgical incision device.

6. A device according to claim 1, wherein said laser source operates at a wavelength between about 800 and 1500 nm.

7. A device according to claim 1, wherein said laser source operates at a wavelength of about 980 nm.

8. A device according to claim 1, wherein laser energy from said laser source is between about 1 W and 10 W.

9. A device according to claim 1, wherein laser energy from said laser source is a continuous wave.

10. A device according to claim 1, wherein laser energy from said laser source is transmitted in high frequency pulses.

11. A device according to claim 1, wherein said optically transparent sharp mechanical cutting edge is selectively coated with a metallic coating to allow light to exit only at desired areas of cauterization.

12. A device according to claim 1 wherein incorporated/ embedded into said optically transparent sharp mechanical cutting edge is at least one optical wave guide.

13. A device according to claim 12 wherein said at least one optical waveguide is directed toward a desired area of cauterization.

14. A device according to claim 12, wherein said optical waveguide is at least one optical fiber.

15. A device according to claim 1, wherein said optically transparent sharp mechanical cutting edge is a removable cutting edge.

16. A device according to claim 15, wherein said removable cutting edge is replaceable with cutting edges that direct radiation in selected directions.

17. A device according to claim 1, wherein said optically transparent sharp mechanical cutting edge is attached to a metal blade.

18. A device according to claim 17 wherein incorporated/ embedded into said metal blade is at least one optical wave guide.

* * * * *